United States Patent [19]

Gautschi

[11] Patent Number: 4,752,361
[45] Date of Patent: Jun. 21, 1988

[54] PROCESS FOR MEASURING THE OXYGEN CONTENT IN THE EXHAUST OF INTERNAL-COMBUSTION ENGINES

[75] Inventor: Max Gautschi, Zürich, Switzerland

[73] Assignee: BBC Brown, Boveri & Company, Ltd., Baden, Switzerland

[21] Appl. No.: 821,340

[22] Filed: Jan. 22, 1986

[30] Foreign Application Priority Data

Feb. 14, 1985 [CH] Switzerland ............... 670/85

[51] Int. Cl.⁴ .................................... G01N 27/46
[52] U.S. Cl. ............................ 204/1 T; 204/424; 204/427; 60/276
[58] Field of Search ........... 204/1 S, 1 T, 421–429; 60/276; 123/440, 489, 589

[56] References Cited

U.S. PATENT DOCUMENTS

| | | | |
|---|---|---|---|
| 3,598,711 | 8/1971 | Flais | 204/427 |
| 3,616,274 | 10/1971 | Eddy | 204/425 |
| 3,869,370 | 3/1975 | Sayles . | |
| 3,907,657 | 9/1975 | Heijne et al. | 204/15 |
| 4,206,173 | 6/1980 | Yamaguchi et al. | 422/98 |
| 4,257,746 | 3/1981 | Wells . | |
| 4,263,883 | 4/1981 | Treible et al. | 204/427 |
| 4,368,431 | 1/1983 | Rohr et al. . | |

FOREIGN PATENT DOCUMENTS 0047434 8/1981 European Pat. Off. .
3316854 8/1984 Fed. Rep. of Germany .

*Primary Examiner*—T. Tung
*Attorney, Agent, or Firm*—Burns, Doane, Swecker & Mathis

[57] ABSTRACT

In this method, the oxygen content in the exhaust is measured relative to the oxygen content of the air by means of a lambda probe (7). To eliminate the influence of pressure variations in the exhaust system (3) of the internal-combustion engine (1) on the measurement, according to the invention an amount of exhaust sample is taken from the exhaust system (3) and not fed to the air pressure of the lambda probe (7) until it has been expanded.

9 Claims, 1 Drawing Sheet

PROCESS FOR MEASURING THE OXYGEN CONTENT IN THE EXHAUST OF INTERNAL-COMBUSTION ENGINES

FIELD OF THE INVENTION

The invention relates to a process for measuring the oxygen content in the exhaust of internal-combustion engines and more particularly to a process of measuring oxygen content of exhaust of internal combustion engines with a lambda probe.

BACKGROUND OF THE INVENTION

For improving the exhaust emissions of internal-combustion engines, exhaust filters are being used to an increasing extent. These filters primarily hold back soot particles but, with appropriate catalytic coating, can also catalytically burn pollutants existing in the exhaust. These filters have the disadvantage, however, that they clog during the course of time due to the accumulated soot, i.e. the flow resistance for the exhaust increases extremely rapidly. It is therefore attempted to burn the collected soot by effecting a constant or a brief increase of the filter temperature. However, there must be adequate oxygen in the exhaust for burning of the soot to take place. For controlling the oxygen content during burning-off and for producing an optimum fuel mixture, a lambda probe is installed between engine and exhaust filter as an oxygen sensor. The measuring signal of the lambda probe is fed to a control system of the internal-combustion engine which acts in a suitable way on the fresh-air supply and/or the amount of fuel. The customary lambda probes have in their measuring head a ceramic element which is provided with two platinum electrodes and is an ion conductor for oxygen. Examples of ion conductors for oxygen are the ceramic materials $ZrO_2$, $TiO_2$, $LaF_3$, $SnO_2$, $Bi_2O_3$, $SrFeO_3$, $La_xSr_{1-x}CrO_3$. If there is a different oxygen content in the exhaust and in the surrounding air, the ceramic element in the measuring head causes a diffusion of oxygen ions, which results in a voltage difference between the two platinum electrodes. This voltage difference is available as a measuring signal.

A lambda probe suitable for measuring the oxygen content in the exhaust of internal-combustion engines relative to the oxygen content of the air, with a $ZrO_2$ ceramic, is known from an article by Hans-Martin Wiedenmann et al., "Heated Zirconia Oxygen Sensor for Stoichiometric and Lean Air-Fuel Ratios", SAE Paper 840141, SAE Congress, Detroit, February-March 1984. The known lambda probe has approximately the shape of a spark plug and can be screwed directly into a bore, provided with an appropriate thread, in a wall of the exhaust system. In the screwed-in state, the ceramic forming the measuring head of the lambda probe protrudes a little into the exhaust chamber. It follows from its functional principle explained above that the measuring signal of the known lambda probe is dependent upon the oxygen partial pressures in the exhaust and in the air. However, the oxygen partial pressure in the exhaust changes with the exhaust pressure. The pressure of the exhaust in the exhaust system of an internal-combustion engine is not constant, but instead depends greatly upon the degree of clogging of the exhaust filter and on the engine speed. In the case of supercharged internal-combustion engines, the pressure variations in the exhaust system are much greater, because the respective charging pressure adds to the influences of the motor speed and the degree of clogging of the exhaust filter. Consequently, the pressure of the exhaust in the exhaust system can vary by a multiple of the air pressure. Under such circumstances the measurement of the percentage oxygen content in the exhaust with a known lambda probe screwed directly into a wall of the exhaust system does not provide usable results. The influence of the exhaust pressure on the measuring signal of the lambda probe could, of course, be eliminated by using a pressure sensor and an electronic calculating unit. such an arrangement however, requires an elaborate design, because the pressure sensor in the exhaust system must be made extremely resistant to corrosion.

OBJECTS AND SUMMARY OF THE INVENTION

The present invention achieves the object of providing a process for measuring the oxygen content in the exhaust of internal-combustion engines with a lambda probe, in which process the influence of the exhaust pressure on the measuring signal of the lambda probe is eliminated in a simple way.

The present invention achieves this object by withdrawing a sample amount of exhaust from an exhaust system and expanding the exhaust sample before communicating it with a lambda probe. The invention includes methods which take exhaust samples continuously or intermittently.

Among the advantages of the process according to the present invention is the capacity to measure oxygen content in an exhaust flow with a lambda probe independent of the pressure in the exhaust system. Accordingly, the present invention avoids the need for measurement of the pressure in the exhaust system and use of electronic calculating devices of the prior art.

The process according to the invention has in all claimed embodiments the advantage that only a small proportion of exhaust is used for measuring the oxygen content in the exhaust. The amount of pollutant contained therein is so negligible that it can in fact be discharged from the measuring chamber directly into the open. On the other hand, the amount of exhaust required for measurement can also be fed to the fresh-air supply system of the internal-combustion engine. In this case, there is in an advantageous way no additional pollutant discharge at all to the surrounding air.

By using a material of low thermal conductivity for the connection of the measuring chamber to the exhaust system, the influence of temperature variations in the exhaust on the measuring signal of the lambda probe can be reduced with particular advantage. The result is of quite considerable significance in the case of internal-combustion engines which are operated with a high oxygen content in the exhaust, and is especially advantageous in the case of diesel engines.

BRIEF DESCRIPTION OF THE DRAWING

The preferred embodiments of the present invention are described below with reference to the drawing, in which.

DETAILED DESCRIPTION OF THE PREFERRED EMBODIMENTS

Figure 1:
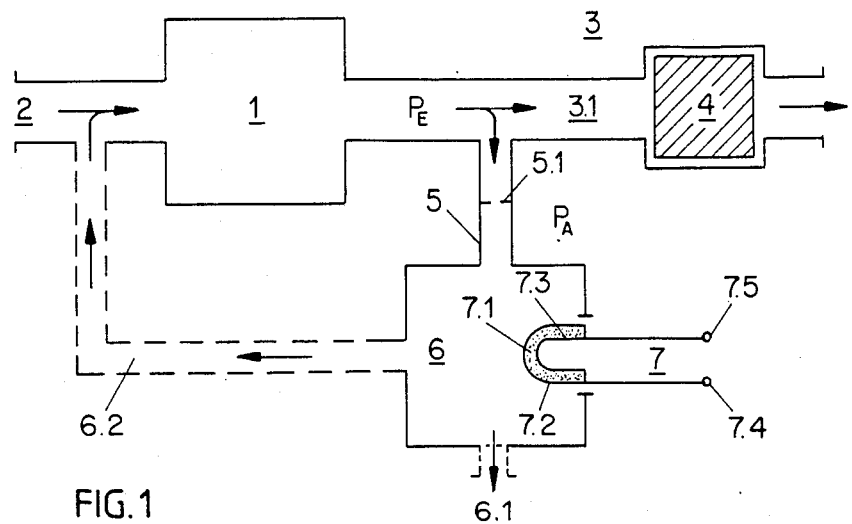
FIG. 1 is a block diagram of a device for implementation of the process according to a preferred embodiment of the present invention the invention with continuous removal of the amount of exhaust sample.

Referring to FIG. 1, an internal-combustion engine 1 receives its fresh air via a fresh-air supply system 2. The exhaust of the internal-combustion engine 1 escapes via an exhaust system 3 in which a soot filter 4 is arranged. Particularly after lengthy use and severe clogging with soot particles, the soot filter 4 represents a considerable flow resistance for the exhaust of the internal-combustion engine 1, so that in the exhaust system 3 between the internal-combustion engine 1 and the soot filter 4 there develops a pressure $P_E$ in the exhaust which is increased relative to the outside air pressure $P_A$. A chamber 6 is connected via a pipe 5 to a part 3.1 of the exhaust system 3 which is under above-atmospheric pressure Chamber 6 is either open to the surrounding air via an orifice 6.1 or is in connection via a pipe 6.2 with the fresh-air supply system 2. Arranged in one wall of the measuring chamber 6 is a lambda probe 7, illustrated diagrammatically. The measuring head of this lambda probe 7 comprises a solid-state electrolyte 7.1, which is provided on its surfaces with platinum electrodes 7.2 and 7.3. The platinum electrode 7.2 is exclusively in contact with the gas in the measuring chamber 6 and the platinum electrode 7.3 is exclusively in contact with the surrounding air. The platinum electrodes 7.2 and 7.3 are finally connected to terminal contacts or terminal clips 7.4 and 7.5, at which the measuring voltage or measuring current of the lambda probe 7 can be picked off. Materials which may be used for the solid-state electrolyte 7.1 are $ZrO_2$, $TiO_2$, $LaF_3$, $SnO_2$, $Bi_2O_3$, $SrFeO_3$ or $La_xSr_{1-x}CrO_3$. However, the first-mentioned zirconia ceramic is preferred.

In the case of the device according to FIG. 1, part of the exhaust from the part 3.1 of the exhaust system 3 under above-atmospheric pressure flows continuously via the pipe 5 into the measuring chamber 6 and expands thereby to a pressure which, on account of the orifice 6.1 or, alternatively, the pipe 6.2 to the fresh-air supply system 2, corresponds approximately to the outside air pressure $P_A$. The lambda probe 7 therefore always determines the oxygen content in the exhaust under constant pressure conditions. The amount of exhaust flowing via the pipe 5 into the measuring chamber 6 depends on the flow resistance of the pipe 5, which is controllable via its cross-section and its length or by built-in baffles 5.1 or porous ceramic elements. The amount of exhaust required for measurement with the lambda probe 7 should be so small in virtually all cases of application that it can readily be released into the surrounding air through the orifice 6.1 without any notable pollution of the surrounding air. If it is desired however to completely avoid the release of unpurified exhaust to the surrounding air, the amount of exhaust required for measurement can be returned via the pipe 6.2 of the internal-combustion engine 1 via its fresh-air supply system 2.

Figure 2:
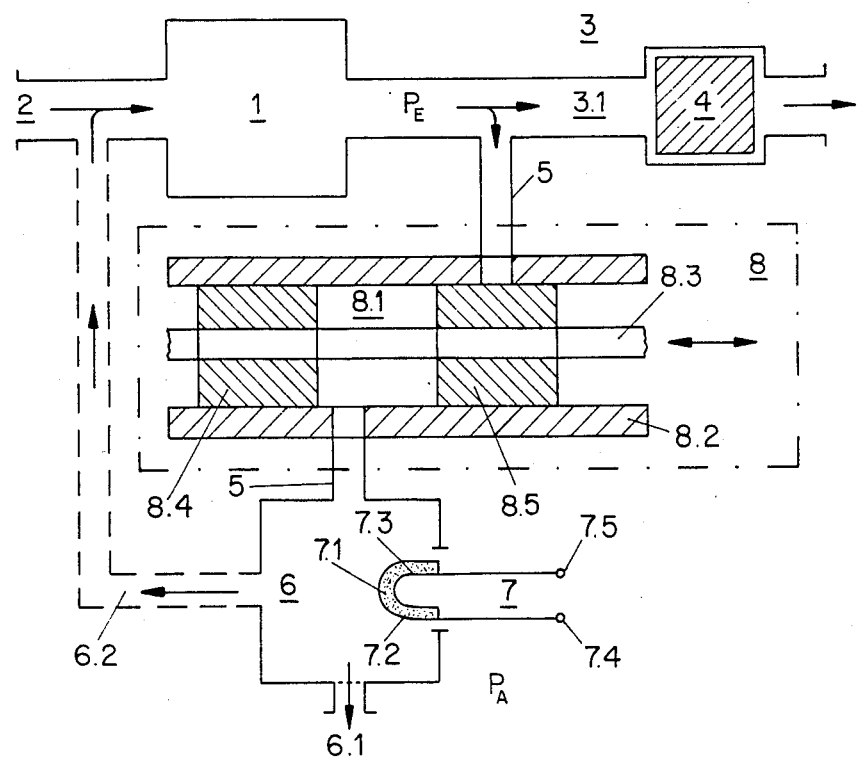
FIG. 2 is a block diagram of a device for implementation of the process according to a second preferred embodiment of the present invention the invention with intermittent removal of the amount of exhaust sample.

Apart from the valve arrangement 8 additionally provided in the pipe 5, the device according to FIG. 2 corresponds to the device according to FIG. 1. The valve arrangement 8 meters the amount of exhaust sample. In the example of FIG. 1 this metering is achieved with continuous flow, as described, via the flow resistance of the pipe 5. However, if the amount of exhaust sample required for measurement is small, appropriately small flow cross-sections in the pipe 5 would have to be provided in the example of FIG. 1. This constitutes the risk of a clogging by soot particles. The valve arrangement 8 provided in FIG. 2 however permits larger cross-sections in the pipe 5 to be used.

If, unlike as shown in FIG. 2, the valve arrangement 8 consists of a single valve, the amount of the exhaust flowing into the measuring chamber 6 depends on the opening duration of this valve.

If, on the other hand, a valve arrangement 8 as shown sectionally in FIG. 2 and which has two valves, bounding an intermediate space 8.1 and each reciprocally opened or closed, is used, the amount of exhaust sample is determined by the size of the intermediate space 8.1, at least when the valves are each opened sufficiently long to make possible a complete pressure equalization between the part 3.1 of the exhaust system 3 and the intermediate space 8.1 and between the latter and the measuring chamber 6.

The valve arrangement 8 shown in FIG. 2 consists simply of a cylinder 8.2 in which two plungers 8.4 and 8.5, connected to each other via a rod 8.3, are movable. The cylinder 8.2 and the plungers 8.4 and 8.5 bound the intermediate space 8.1. The cylinder 8.2 has in its wall two orifices for connection of the pipe 5. These orifices are mutually offset with respect to the longitudinal axis of the cylinder 8.2. By displacement of the two plungers 8.4 and 8.5, the intermediate space 8.1 can be opened alternatively to the part 3.1 of the exhaust system 3 and to the measuring chamber 6. The rod 8.3 could be driven via a control rod, for example by the camshaft of the internal-combustion engine 1.

By use of the valve arrangement 8, the removal of the amount of exhaust sample from the exhaust system 3 is discontinuous.

In the case of lambda probes 7 of the type used here, the diffusion of the oxygen through the solid-state electrolyte 7.1, and thus also the measuring signal, is highly temperature-dependent. To achieve a good measuring result, it is therefore necessary to keep the temperature of the solid-state electrolyte 7.1 constant at a value at the upper limit of the exhaust temperatures occurring, for example by a heating system integrated in the lambda probe. By using a poorly thermally conductive material for the connection between the exhaust system 3 and measuring chamber 6, particularly for the pipe 5, this requirement can be met considerably more easily. Stainless steel has an adequately low thermal conductivity, for example. By this measure, a further improvement of the measurement of the oxygen content in the exhaust is achieved in an advantageous way.

It is to be understood that the present invention may be embodied in other specific forms without departing from the spirit or essential characteristics of the present invention. The preferred embodiments are therefore to be considered illustrative and not restrictive. The scope of the invention is indicated by the appended claims rather than by the foregoing descriptions and all changes or variations which fall within the meaning and range of the claims are therefore intended to be embraced therein.

What is claimed is:

1. A process for measuring oxygen content in the exhaust at a location along an exhaust system of an internal-combustion engine relative to the oxygen content of ambient air outside of the exhaust system with a probe operative by oxygen diffusion in solid-state electrolytes, said location being subject to above-ambient pressure, said process comprising the steps of:

withdrawing a sample amount of exhaust from the exhaust system at said location, expanding the exhaust sample to ambient pressure into a chamber that is open to the ambient air outside of the engine or to a fresh-air supply system of the internal-combustion engine, said chamber having a wall in which a solid state electrolyte of the probe is arranged and, then communicating the expanded exhaust sample with the probe.

2. The process according to claim 1, wherein said sample withdrawing step includes communicating a pipe with said exhaust system at said location and restricting exhaust flow through said pipe with a constriction.

3. The process according to claim 2, wherein said constriction is formed with a baffle or a porous ceramic element at a location along said pipe.

4. The process according to claim 2, further comprising the step of utilizing a material of low thermal conductivity for communicating said location to the chamber.

5. The process according to claim 1, wherein said withdrawing step includes intermittent opening of a valve which is in communication with said location.

6. The process according to claim 1, wherein the solid-state electrolyte in the probe is selected from the group consisting of $ZrO_2$, $TiO_2$, $LaF_3$, $SnO_2$, $Bi_2O_3$, $SrFeO_3$ and $La_xSr_{1-x}CrO_3$.

7. A process for measuring oxygen content in the exhaust at a location along an exhaust system of an internal-combustion engine relative to the oxygen content of ambient air outside of the exhaust system with a probe operative by oxygen diffusion in solid-state electrolytes, said location being subject to above-ambient pressure, said process comprising the steps of:

withdrawing a sample amount of exhaust from the exhaust system at said location, expanding the exhaust sample to ambient pressure, and then communicaing the expanded exhaust sample with the probe, wherein said steps include opening a first valve which is in communication with said location and expanding the exhaust sample withdrawn through said first valve into an enclosed intermediate space, closing the first valve, after said closing, opening a second valve which is in communication with said intermediate space and expanding the exhaust sample into a chanmber which is open to the ambient air outside the engine or to a fresh-air supply system of the internal-combustion engine, said chamber having a wall in which a solid-state electrolyte of the probe is arranged.

8. The process according to claim 7, wherein the intermediate space is formed by two plungers rigidly connected to each other in a cylinder, said intermediate space opened or closed relative to either the exhaust system or the chamber by displacement of the plungers in the cylinder.

9. The process according to claim 8, wherein the plungers are driven by a camshaft of the internal-combustion engine.

* * * * *